United States Patent [19]

Schönafinger et al.

[11] Patent Number: 4,760,147
[45] Date of Patent: Jul. 26, 1988

[54] OPTICALLY ACTIVE, SUBSTITUTED 1,4-DIHYDROPYRIDINES AND THEIR USE AS MEDICAMENTS

[75] Inventors: Karl Schönafinger, Alzenau; Helmut Bohn, Schöneck; Piero Martorana, Bad Homburg; Rolf-Eberhard Nitz, Frankfurt, all of Fed. Rep. of Germany

[73] Assignee: Cassella Aktiengesellschaft, Fed. Rep. of Germany

[21] Appl. No.: 941,176

[22] Filed: Dec. 12, 1986

Related U.S. Application Data

[62] Division of Ser. No. 759,296, Jul. 26, 1985.

[30] Foreign Application Priority Data

Aug. 24, 1984 [DE]  Fed. Rep. of Germany ....... 3431152

[51] Int. Cl.[4] .............................................. C07D 413/04
[52] U.S. Cl. ...................................... 546/277; 546/278; 546/279; 546/270
[58] Field of Search ............... 546/276, 277, 278, 279, 546/270; 514/333, 340, 341, 342, 338

[56] References Cited

U.S. PATENT DOCUMENTS

| 4,497,808 | 2/1985 | Zimmermann et al. | 546/276 |
| 4,510,310 | 4/1985 | Wehinger et al. | 546/270 |
| 4,532,248 | 7/1985 | Franckowiak et al. | 514/320 |
| 4,551,467 | 11/1985 | Wehinger et al. | 546/257 |
| 4,558,058 | 12/1985 | Schönafinger et al. | 546/256 |
| 4,578,467 | 3/1986 | Bonacchi et al. | 514/252 |

OTHER PUBLICATIONS

Schramm et al., Nature, vol. 303, Jun. 9, 1983.

Primary Examiner—Jane T. Fan
Attorney, Agent, or Firm—Perman & Green

[57] ABSTRACT

Optically active substituted 1,4-dihydropyridines of the formula I having calcium antogonistic properties:

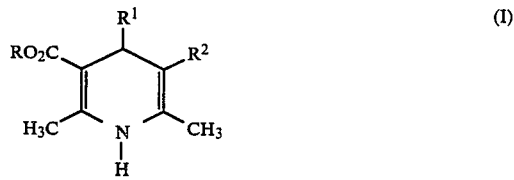

wherein
R denotes alkyl with 1 to 5 C atoms, alkoxy-alkyl with 1 to 4 C atoms, in the alkoxy part and 2 to 4 C atoms in the alkyl part, dialkylaminioalkyl with a total of 3 to 6 C atoms each of the alkyl groups as substituents on the amino group having 1 to 3 C atoms, or —CH(CH$_3$)CO$_2$R$^5$ in the optically active (R)-forms,
R$^1$ denotes phenyl which is monosubstituted by cyano, nitro or chlorine or is disubstituted by chlorine, R$^2$ denotes oxadiazolyl, or an oxadiaxolyl which is substituted by methyl, ethyl, i-propyl, tert.-butyl, benzyl, methylthio, i-propylthio, aminocarbonylthio or methoxymethyl,
R$^5$ denotes alkyl with 1 to 4 C atoms, and acid-addition salts thereof, and acid addition salts thereof.

6 Claims, No Drawings

OPTICALLY ACTIVE, SUBSTITUTED 1,4-DIHYDROPYRIDINES AND THEIR USE AS MEDICAMENTS

This is a divisional of co-pending application Ser. No. 759,296, filed on July 26, 1985.

The invention relates to a process for the preparation of optionally active, substituted 1,4-dihydropyridines of the formula

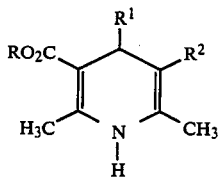

and their acid addition salts, wherein, in formula I, R denotes the radical $R^3$ or $R^4$, $R^1$ denotes pyridyl or thienyl, the pyridyl or thienyl radical optionally carrying 1 or 2 identical or different substituents from the group comprising alkyl with 1 to 4 C atoms, alkoxy with 1 to 4 C atoms, halogen, trifluoromethyl, nitro and cyano; or denotes phenyl, which optionally carries 1 or 2 identical or different substituents from the group comprising halogen, nitro, cyano, trifluoromethyl, alkyl with 1 to 4 C atoms and alkoxy with 1 to 4 C atoms, $R^2$ denotes the radical of a 5-membered ring with at least one double bond and at least 2 hetero-atoms or hetero-atom groupings from the series comprising O, N, NH and S, the 5-membered ring optionally carrying 1 or 2 identical or different substituents from the group comprising alkyl with 1 to 4 C atoms, alkylthio with 1 to 4 C atoms, aralkyl with a total of 7 to 9 C atoms, alkoxyalkyl with a total of 2 to 5 C atoms, cycloalkyl with 5 or 6 atoms, aminocarbonylmethylthio, methoxycarbonyl, ethoxycarbonyl and phenyl, $R^3$ denotes alkyl with 1 to 6 C atoms, alkoxyalkyl with 3 to 8 C atoms, dialkylaminoalkyl with a total of 4 to 9 C atoms, N-aralkyl-N-alkyl-aminoalkyl with a total of 10 to 14 C atoms or cycloalkyl with 5 or 6 C atoms, $R^4$ denotes the radical (R)—$CH(CH_3)CO_2R^5$, (S)—$CH(CH_3)CO_2R^5$ or the radical of formula II

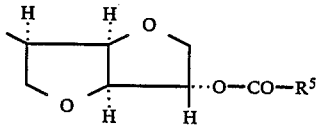

and $R^5$ denotes alkyl with 1 to 6 C atoms.

The invention also relates to the optically active compounds of the formula I and their use as medicaments.

The alkyl and alkoxy radicals mentioned, also when they occur in combination with one another or in other radicals, such as, for example, alkoxyalkyl, aralkyl, dialkylaminoalkyl and alkoxycarbonyl, or as substituents of other radicals, are straight-chain or branched. Where ranges for their carbon number have not already been given above for them or for the groupings containing them, they usually contain 1 to 4 C atoms.

The aralkyl radicals mentioned are, in particular, phenalkyl radicals, thus, for example, phenylpropyl, phenethyl or benzyl, of which phenethyl and, in particular, benzyl are preferred.

Halogen as a rule denotes chlorine, bromine or fluorine, preferably chlorine or bromine, and especially preferably chlorine.

$R^1$ can be, for example, a 2-, 3- or 4-pyridyl radical or a 2- or 3-thienyl radical, it being possible for these radicals to carry one or two identical or different sustituents.

$R^1$ preferably denotes phenyl, which optionally carries one or two identical or different substituents, preferably from the series comprising chlorine, bromine, fluorine, nitro, cyano, methyl, methoxy and trifluoromethyl. Examples of such radicals $R^1$ are: phenyl, 2-chlorophenyl, 3-chlorophenyl, 4-chlorophenyl, 2,3-dichlorophenyl, 2-nitrophenyl, 3-nitrophenyl, 3-cyanophenyl, 3-methoxyphenyl, 3-trifluoromethylphenyl, 2-trifluoromethylphenyl, o-tolyl, m-tolyl and p-tolyl.

$R^1$ particularly preferably denotes a phenyl radical which is monosubstituted by cyano, nitro or chlorine or disubstituted by chlorine, the substituents preferably being in the 2- and/or 3-position of the phenyl nucleus. $R^1$ very particularly preferably denotes 2-nitrophenyl, 3-nitrophenyl, 3-cyanophenyl, 2-chlorophenyl and 2,3-dichlorophenyl.

$R^2$ can be, for example, an oxazolyl, thiazolyl, imidazolyl, triazolyl, oxadiazolyl or thiadiazolyl radical. Examples of possible substituents for these radicals $R^2$ are: methyl, ethyl, n-propyl, i-propyl, n-butyl, i-butyl, tert.-butyl, benzyl, methylthio, i-propylthio, methoxymethyl, 2-methoxyethyl, aminocarbonylmethylthio, methoxycarbonyl, ethoxycarbonyl, cyclopentyl, cyclohexyl and phenyl. Of the 5-membered rings which represent radicals $R^2$, those which contain two nitrogen atoms and one oxygen atom and two double bonds are preferred, such as, for example, 1,3,4-oxadiazol-2-yl, 1,2,4-oxadiazol-5-yl and 1,2,4-oxadiazol-3-yl. Preferred substituents are: methyl, ethyl, i-propyl, tert.-butyl, benzyl, methylthio, i-propylthio, aminocarbonylmethylthio and methoxymethyl. Particularly preferred substituents are: methyl, ethyl and benzyl. 1,3,4-Oxadiazol-2-yl, 5-methyl-1,3,4-oxadiazol-2-yl, 5-ethyl-1,3,4-oxadiazol-2-yl, 3-methyl-1,2,4-oxadiazol-5-yl, 3-ethyl-1,2,4-oxadiazol-5-yl and 3-benzyl-1,2,4-oxadiazol-5-yl are particularly preferred for $R^2$.

In the N-aralkyl-N-alkyl-aminoalkyl radical $R^3$, the N-aralkyl-N-alkykl-amino group is, in particular, on the terminal C atom of the alkyl radical, such as, for example: 2-(N-benzyl-N-methyl-amino)-ethyl, 2-(N-phenethyl-N-methylamino)-ethyl and 2-(N-benzyl-N-ethyl-amino)-ethyl.

$R^3$ preferably denotes alkyl with 1 to 5 C atoms, alkoxyalkyl with 1 to 4 C atoms in the alkoxy part and 2 to 4 C atoms in the alkyl part or dialkylaminoalkyl with a total of 3 to 6 C atoms, it being possible for each of the alkyl groups as substituents on the amino group to have 1 to 3 C atoms and the alkoxy group in the alkoxyalkyl radical and the dialkylamino group in the dialkylaminoalkyl radical being, in particular, on the terminal C atom of the alkyl radical. Examples of such preferred radicals $R^3$ are: methyl, ethyl, n-propyl, i-propyl, n-butyl, i-butyl, sec.-butyl, tert.-butyl, neopentyl, 2-methoxyethyl, 2-i-propoxyethyl, 2-n-butoxyethyl, 3-methoxy-n-propyl and 2-dimethylaminoethyl. $R^3$ particularly preferably denotes methyl, n-propyl, n-butyl, i-butyl, tert.-butyl and 2-i-propoxyethyl. $R^3$ very particularly preferably denotes i-propyl or 2-methoxyethyl.

The radical $R^4$ represents the radical —$CH(CH_3)CO_2R^5$ in the optically active (R)- or (S)-form which derives from an optically active (R)- or (S)-lactic acid ester of the formula HO-CH(CH₃)CO₂R⁵. (Throughout the description and the claims the expression (R) means "rectus", right and (S) means "sinister", left.) Moreover, the radical R⁴ preferably represents a radical of the formula II

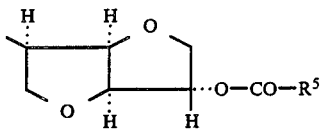

which derives from a 2-O-(R⁵-carbonyl)-isosorbide of the formula IIa

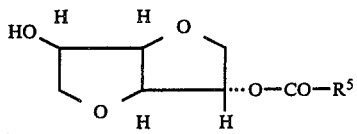

The compound, which in formula IIa possesses an -H instead of the radical —CO—R⁵ and thus has the formula IIb

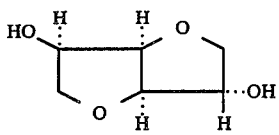

is designated, for example, isosorbide, 1.4:3.6-dianhydro-D-glucitol or 1.4:3.6-dianhydro-D-sorbite. Within the scope of the present invention the optically active radical of formula II is termed, for simplicity's sake, 2-O-(R⁵-carbonyl)-isosorbid-5-yl.

R⁵ preferably represents alkyl with 1 to 4 C atoms, in particular methyl or ethyl. The radical R⁵ in formula II preferably denotes methyl, so that the radical 2-O-acetyl-isosorbid-5-yl is particularly preferred for II.

Preferred compounds of the formula I are those in which the radicals have one or, in particular, more of the preferred meanings mentioned. Very particularly preferred compounds are those in which the radicals have one or, in particular, more, preferably all, of the particularly preferred meanings given.

Compounds of the formula I where R=R⁴ are designated below as compounds of the formula Ia, and compounds of the formula I where R=R³ are designated below as compounds of the formula Ib:

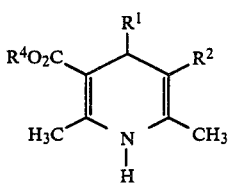

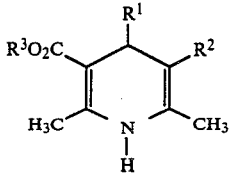

Optically inactive compounds of the formula Ib are described in the European Patent Application with the Application Number 83112562.0, Publication Number 0116708 and corresponding U.S. Pat. No. 4,558,058 which issued on Dec. 10, 1985. It has now been found that the optically active compounds of the formula Ib can be obtained in an elegant manner by a process in which an optically active compound of the formula Ia is transesterified with an alcohol of the formula R³OH:

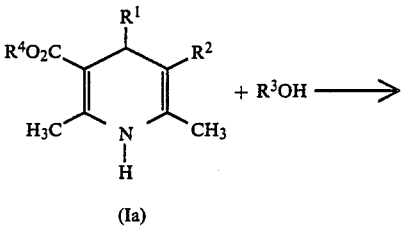

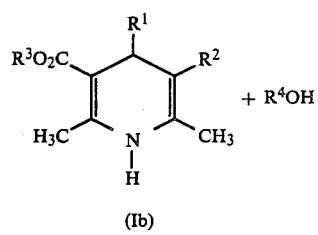

This transesterification is carried out in a manner which is known per se. At least 1 mole of alcohol of the formula R³OH is employed per mole of the compound Ia. As a rule, 1.2 to 50 moles, preferably 1.5 to 30 moles, of R³OH are employed per mole of the compound of the formula Ia and the transesterification is carried out at normal temperature or, advantageously, at elevated temperature and advantageously in the presence of a transesterification catalyst. If excess alcohol R³OH does not serve as the solvent, it is advantageous to use a suitable inert solvent. Examples of suitable inert solvents are: ethers, in particular those with 2 to 8 C atoms in the molecule, such as, for example, diethyl ether, methyl ethyl ether, di-n-propyl ether, di-iso-propyl ether, methyl n-butyl ether, ethyl propyl ether, dibutyl ether, tetrahydrofuran, 1,4-dioxane, 1,2-dimethoxyethane and bis-β-methoxyethyl ether; aliphatic hydrocarbons, such as, for example, low-boiling and high-boiling petroleum ethers; aromatic hydrocarbons, such as, for example, benzene, toluene, o-, m- and p-xylene and pyridine; and halogenated aliphatic or aromatic hydrocarbons, such as, for example, methylene chloride, carbon tetrachloride, ethylene chloride, chlorobenzene and dichlorobenzene. Mixtures of various solvents can also be used.

The choice of the alcohol R³OH is determined by the meanings of R³ already mentioned, so that the alcohol R³OH used is: an alkanol with 1 to 6 C atoms, an alkoxyalkanol with 3 to 8 C atoms, a dialkylaminoalkanol with a total of 4 to 9 C atoms, an N-aralkyl-N-alkyl-aminoalkanol with a total of 10 to 14 C atoms, cyclopentanol or cyclohexanol. The preferred alcohols $R^3OH$ correspondingly derive from the preferred radicals $R^3$ and the particularly preferred alkohols $R^3OH$ derive from the particularly preferred radicals $R^3$. The following examples are preferred alcohols $R^3OH$: methanol, ethanol, N-propanol, i-propanol, n-butanol, i-butanol, sec.-butanol, tert.-butanol, neopentanol, 2-methoxy-ethanol; 2-i-propoxy-ethanol, 2-n-butoxy-ethanol, 3-methoxy-n-propanol, and 2-dimethylamino-ethanol. Methanol, n-propanol, n-butanol, i-butanol, tert.-butanol and 2-i-propoxy-ethanol are particularly preferred. I-propanol and 2-methoxy-ethanol are very particularly preferred.

Possible elevated temperatures for the transesterification are temperatures up to the reflux temperature and, in particular if an excess of the alcohol $R^3OH$ is used as solvent, in particular, the reflux temperature. However, in some cases, in particular also if an excess of the alcohol $R^3OH$ is used as solvent, it is advantageous to carry out the transesterification at a temperature which under normal pressure is above the reflux temperature for example by up to 50° C. or more, because the yield and/or purity of the transesterification product are in some cases considerably increased thereby. Transesterification at a temperature which is above the reflux temperature is carried out in a pressure vessel under the autogenous pressure of the reaction.

Taking into consideration the above circumstances the transesterification is, in general, carried out at temperatures of from 50° to 190° C., preferably 60° to 150° C.

Possible suitable transesterification catalysts are the known transesterification catalysts, thus, for example, acids or, in particular, bases. Examples of acids which are suitable as transesterification catalysts are inorganic acids, such as, for example, hydrogen halide acids, such as, for example, hydrogen chloride and hydrogen bromide, sulphuric acid, organic sulphonic acids, such as, for example, benzene- or p-toluene-sulphonic acid, and strong organic acids, such as, for example, trifluoroacetic acid, and the like.

Examples of suitable basic transesterification catalysts are alkali metal or alkaline earth metal salts of monocarboxylic acids, in particular those with 1 to 4 C atoms, and furthermore alkali metal hydroxides, such as, for example, lithium hydroxide, sodium hydroxide or potassium hydroxide, and alkali metal carbonates, such as, for example, sodium carbonate or potassium carbonate. The alkali metal, alkaline earth metal, aluminium, titanium and germanium compounds of the alcohols $R^3OH$ are also particularly suitable, thus, for example, the sodium, potassium, lithium, magnesium, calcium, aluminium or titanium compounds of the alcohols $R^3OH$.

It is not absolutely necessary to use these alcoholates in isolated form, but as, for example, in the case of the alkali metal or alkaline earth metal alcoholates, they can frequently be formed from the alcohol $R^3OH$ and the corresponding alkali metal or alkaline earth metal. In some cases, tin salts, manganese salts, tin(IV) oxide and antimony trioxide can also be used as transesterification catalysts. It is also possible to use mixtures of two or more suitable transesterification catalysts.

The amount of transesterification catalyst added is kept as low as possible. As a rule, 0.01 to 1.1 moles, preferably 0.02 to 1.0 mole, of transesterification catalyst are sufficient. Preferred transesterification catalysts are the basic transesterification catalysts mentioned, in particular the alkali metal salts, above all the lithium, sodium or potassium salts, of the alcohols $R^3OH$. A particularly preferred alcohol $R^3OH$ for the transesterification is isopropanol, especially in the presence of lithium isopropanolate, potassium isopropanolate or sodium isopropanolate as a transesterification catalyst. Another particularly preferred alcohol $R^3OH$ for the transesterification is 2-methoxy-ethanol, in particular in the presence of lithium 2-methoxy-ethanolate, potassium 2-methoxy-ethanolate or sodium 2-methoxy-ethanolate as a transesterification catalyst.

If desired, the optically active compound Ib obtained in the transesterification is converted into an acid addition salt in a manner which is known per se.

Several processes are possible for the preparation of the compounds of the formula Ia (R denotes $R^4$ in formula I), in the pure optically active form required for the transesterification. Advantageously, the substituted, optically active 1,4-dihydropyridines of the formula Ia are prepared by a process analogous to the preparation of other 1,4-dihydropyridine compound, in which (a) 1 mole of an ylidene compound of the formula III

and 1 mole of a 3-aminocrotonic acid ester of the formula IV

or in which, (b) 1 mole of an aldehyde of the formula V

1 mole of a 3-aminocrotonic acid ester of the formula IV

and 1 mole of a ketone of the formula VI

or in which, (c) 1 mole of an ylidene compound of the formula III

1 mole of an acetoacetic acid ester of the formula VII

and 1 mole of ammonia ($NH_3$), or in which, (d) 1 mole of an ylidene compound of the formula VIII

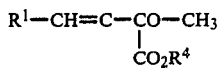

(VIII)

and 1 mole of an enamine of the formula IX

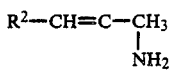

or in which,
(e) 1 mole of an aldehyde of the formula V

     (V)

1 mole of an acetoacetic acid ester of the formula VII

     (VII)

1 mole of a ketone of the formula VI

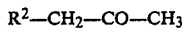     (VI)

and 1 mole of ammonia (NH₃), or in which,
(f) 1 mole of an aldehyde of the formula V

     (V)

1 mole of an acetoacetic acid ester of the formula VII

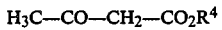     (VII)

and 1 mole of an enamine of the formula IX

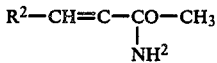     (IX)

are reacted with one another, $R^1$, $R^2$ and $R^4$ in the compounds of the formulae III to IX having the meanings mentioned initially, and in which a pure optically active compound is isolated from the diastereomer mixtures thus obtained and, if appropriate, is converted into an acid addition salt.

On the basis of the fact that the radical $R^4$ exhibits optical activity, the compounds of the formulae IV, VII and VIII are themselves optically active. In the preparation of the compounds of the formula Ia, the compounds of the formulae IV, VII and VIII are employed in the form of the pure optically active compounds. However, starting from the compounds of the formulae III to IX, there are also other possible synthesis processes for the com-pounds of the formula Ia. The process variants are variants or part steps of the known Hantzsch pyridine synthesis.

The reaction for the preparation of the compounds Ia is carried out at room temperature (20° C.) or, in particular, elevated temperature, for example in a range from 20° to 160° C., preferably 40° to 120° C., in all the variants (a) to (f). The reaction is usually carried out under normal pressure, but can also be carried out under a pressure which deviates from normal pressure.

The reactions are carried out in water or an inert organic solvent. Examples of suitable solvents are alcohols, in particular those with 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example, diethyl ether, methyl ethyl ether, di-n-propyl ether, di-iso-propyl ether, methyl n-butyl ether, ethyl propyl ether, di-butyl ether, tetrahydrofuran, 1,4-dioxane, 1,2-dimethoxyethane and bis-β-methoxyethyl ether; polyethers, such as, for example, polyethylene glycols with a molecular weight of up to about 600; oligoethylene glycol dimethyl ethers, such as, for example, pentaglyme; glycols and partially etherified glycols, such as, for example, ethylene glycol, propylene glycol, trimethylene glycol, ethylene glycol monomethyl ether, ethylene glycol monoethyl ether and diethylene glycol monoethyl ether; ketones, in particular those with 3 to 10 C atoms in the molecule, such as, for example, acetone, methyl ethyl ketone, methyl n-propyl ketone, diethyl ketone, 2-hexanone, 3-hexanone, di-n-propyl ketone, di-iso-propyl ketone, di-iso-butyl ketone, cyclopentanone, cyclohexanone, benzophenone and acetophenone; aliphatic hydrocarbons, such as, for example, low-boiling and high-boiling petroleum ethers; aromatic hydrocarbons, such as, for example, benzene, toluene, o-, m- and p-xylene and pyridine; halogenated aliphatic or aromatic hydrocarbons, such as, for example, methylene chloride, chloroform, carbon tetrachloride, ethylene chloride, chlorobenzene or dichlorobenzene; nitriles, such as, for example, acetonitrile; amides, such as, for example, dimethylformamide, N-methyl-pyrrolidone and hexamethylphosphoric acid triamide; sulphoxides, such as, for example, dimethylsulphoxide; and water. Mixtures of various solvents can also be used. Alcohols or mixtures of alcohols with water are as a rule preferred.

Of the abovementioned process variants for the preparation of the compounds of the formula Ia, process variant (a) is preferred.

The starting substances of the formulae III to IX required for the preparation of the compounds of the formula Ia are known or can easily be prepared by the processes known for the particular class of compound.

If they are not already known, the compounds of the formula IX can be prepared, for example, in accordance with the method of A. C. Cope, J. Amer. chem. Soc. 67, 1017 (1945). Examples which may be mentioned of enamino compounds of the formula IX are: 2-(2-aminopropen-1-yl)-4-methyl-5-ethoxycarbonylthiazole, 2-(2-aminopropen-1-yl)-thiazole, 2-(2-aminopropen-1-yl)-4-phenyl-thiazole, 5-(2-aminopropen-1-yl)-3-methyl-1,2,4-oxadiazole, 5-(2-aminopropen-1-yl)-3-ethyl-1,2,4-oxadiazole, 5-(2-aminopropen-1-yl)-3-tert.-butyl-1,2,4-oxadiazole, 5-(2-aminopropen-1-yl)-3-benzyl-1,2,4-oxadiazole, 2-(2-aminopropen-1-yl)-1,3,4-oxadiazole, 2-(2-aminopropen-1-yl)-5-aminocarbonylmethylthio-1,3,4-oxadiazole, 2-(2-aminopropen-1-yl)-5-methyl-1,3,4-oxadiazole, 3-(2-aminopropen-1-yl)-1,2,4-oxadiazole, 3-(2-aminopropen-1-yl)-5-methyl-1,2,4-oxadiazole, 3-(2-aminopropen-1-yl)-5-benzyl-1,2,4-oxadiazole, 5-(2-aminopropen-1-yl)-1,2,4-thiadiazole and 5-(2-aminopropen-1-yl)-3-methylthio-1,2,4-thiadiazole.

If they are not already known, the aldehydes of the formula V used as starting components can be prepared, for example, by the methods described by E. Mosettig, Org. Reactions VIII, 218 et seq. (1954). Examples of suitable aldehydes of the formula V are: benzaldehyde, 2-, 3- or 4-methyl-benzaldehyde, 2-, 3- or 4-ethyl-benzaldehyde, 2-, 3- or 4-i-propyl-benzaldehyde, 2-, 3- or 4-tert.-butyl-benzaldehyde, 2-, 3- or 4-methoxy-benzaldehyde, 2-, 3- or 4-i-propoxy-benzaldehyde, 2-, 3- or 4-bromo-benzaldehyde, 2-, 3- or 4-chloro-benzaldehyde, 2-, 3- or 4-fluoro-benzaldehyde, 2-, 3- or 4-cyano-benzaldehyde, 2-, 3- or 4-trifluoromethylbenzaldehyde, 2-, 3- or 4-nitro-benzaldehyde, 2,4- or 2,6-dimethylbenzaldehyde, 2,4- or 2,6-dichloro-benzaldehyde, 2,4- or 2,6-dibromo-benzaldehyde, 2,4- or 2,6-dinitro-benzaldehyde, 2,4- or 2,6-diethylbenzaldehyde, 3-chloro-4-trifluoromethyl-benzaldehyde, 3-methyl-4-trifluoromethyl-benzaldehyde, 3-methoxy-4-chloro-benzaldehyde, 2-methyl-4-cyano-benzaldehyde, pyridine-2-aldehyde, pyridine-3-aldehyde, pyridine-4-aldehyde, 4-methyl-pyridine-2-aldehyde, 5-methylpyridine-2-aldehyde, 6-methyl-pyridine-2-aldehyde, thiophene-2-aldehyde, thiophene-3-aldehyde, 5-nitro-thiophene-2-aldehyde, 5-methyl-thiophene-2-aldehyde, 5-chloro-thiophene-2-aldehyde and 5-methoxy-thiophene-2-aldehyde.

If they are not already known, the pure optically active derivatives of acetoacetic acid required as starting compounds of the formula VII can easily be prepared by reacting an (R)- or (S)-lactic acid ester of the formula (R)— or (S)—HO—CH(CH$_3$)CO$_2$R$^5$ or a 2—O—(R$^5$-carbonyl)-isosorbide of the formula IIa with diketene. Such reactions are described in the examples which follow. Other compounds of the formula VII can be prepared analogously.

If they are not already known, the ylidene compounds of the formulae III and VIII required as starting components can be prepared in accordance with Org. Reactions XV, 204 et seq. (1967). Examples of suitable starting compounds of the formula III are: 1-(2,3-dichlorophenyl)-2-(1,3,4-oxadiazol-2-yl)-1-buten-3-one, 1-(3-nitrophenyl)-2-(1,3,4-oxadizol-2-yl)-1-buten-3-one, 1-(2-chlorophenyl)-2-(1,3,4-oxadiazol-2-yl)-1-buten-3-one, 1-(3-cyanophenyl)-2-(1,3,4-oxadiazol-2-yl)-1-buten-3-one, 1-(pyridin-3-yl)-2-(1,3,4-oxadiazol-2-yl)-1-buten-3-one, 1-(thien-2-yl)-2-(1,3,4-oxadiazol-2-yl)-1-buten-3-one, 1-(3-trifluoromethylphenyl)-2-(1,3,4-oxadiazol-2-yl)-1-buten-3-one, 1-(2,3-dichlorophenyl)-2-(2-methyl-1,3,4-oxadiazol-5-yl)-1-buten-3-one, 1-(2,3-dichlorophenyl)-2-(2-benzyl-1,3,4-oxadiazol-5-yl)-1-buten-3-one, 1-(2-methylphenyl)-2-(3-ethyl-1,2,4-oxadiazol-5-yl)-1-buten-3-one, 1-(3-methoxyphenyl)-2-(3-tert.-butyl-1,3,4-oxadiazol-5-yl)-1-buten-3-one, 1-(3-chlorophenyl)-2-(1,2,4-thiadiazol-5-yl)-1-buten-3-one, 1-(2-trifluoromethyl)-2-(3-benzyl-1,2,4-oxadiazol-5-yl)-1-buten-3-one, 1-(2,5-dichlorophenyl)-2-(3-methylthio-1,3,4-oxadiazole)-1-buten-3-one, 1-(pyridin-2-yl)-2-(4-methyl-5-ethoxycarbonyl-thiazol-2-yl)-1-buten-3-one, 1-(3-nitrophenyl)-2-(3-methyl-1,2,4-oxadiazol-5-yl)-1-buten-3-one and 1-(2,3-dichlorophenyl)-2-(3-ethyl-1,2,4-oxadiazol-5-yl)-1-buten-3-one.

The ylidene compounds of the formula VIII can be prepared in the pure optically active form by a process in which the above-mentioned optically active compounds of the formula VII are subjected to a condensation reaction with aldehydes of the formula V by known processes.

The 3-aminocrotonic acid ester derivatives of the formula IV can easily be prepared in the pure optically active form by a process in which pure optically active acetoacetic acid ester derivatives of the formula VII are converted into aminocrotonic acid derivatives with ammonia in a manner which is known per se. Such reactions are described in the examples which follow. Other compounds of the formula IV can be prepared analogously.

If they are not already known, the ketones of the formula VI can be prepared by the process described in Monatshefte fur Chemie 113, 781 et seq. (1982). Examples of suitable starting compounds of the formula VI are 5-acetonyl-1,2,4-oxadiazole, 3-methyl-5-acetyl-1,2,4-oxadiazole, 3-ethyl-5-acetyl-1,2,4-oxadiazole, 3-tert.-butyl-5-acetyl-1,2,4-oxadiazole, 3-methylthio-5-acetyl-1,2,4-oxadiazole, 3-benzyl-5-acetyl-1,2,4-oxadiazole, 2-acetonyl-1,3,4-oxadiazole, 5-methyl-2-acetonyl-1,3,4-oxadiazole, 5-i-propyl-2-acetonyl-1,3,4-oxadiazole, 3-acetonyl-1,2,4-oxadiazole, 5-ethyl-3-acetonyl-1,2,4-oxadiazole, 5-ethylthio-3-acetonyl-1,2,4-oxadiazole, 5-phenethyl-3-acetonyl-1,2,4-oxadiazole, 5-acetonyl-1,2,4-thiadiazole, 3-ethyl-5-acetonyl-1,2,4-thiadiazole and 3-benzyl-5-acetonyl-1,2,4-thiadiazole.

The compounds of the formula Ia which can be prepared by processes (a) to (f) have asymmetric carbon atoms in the radical R$^4$ and in the 4-position of the dihydropyridine nucleus, and are therefore formed by processes (a) to (f) in the form of mixtures of diastereomers. Surprisingly, it has been found that when processes (a) to (f) are carried out in practice, crude mixtures of diastereomers are obtained in which in each case one diastereomer is present in excess. On the basis of the different distribution of the diastereomers in the resulting crude mixtures and the different physical properties of the diastereomers, a diastereomer can be isolated in an optically pure form from the crude mixtures obtained in reactions (a) to (f). A number of separation or purification processes are available for this isolation, such as, for example, chromatography, extraction or recrystallisation. Depending on the separation process used and the physical properties of the diastereomers, it is easier to isolate either the diastereomer present in the minor amount or that present in the major amount. It is also possible to isolate both diastereomers in a pure form. As a rule, a diastereomer of the formula Ia present in the crude mixture is isolated in the optically active pure form by recrystallisation, the diastereomer present as the main product in excess in the crude mixture generally being isolated. As a rule, only a single recrystallisation is necessary to isolate the compound in a pure optically active form. The usual solvents are suitable for this recrystallisation, in particular alcohols with 1 to 4 C atoms, such as, for example, methanol, ethanol, propanol, isopropanol, butanol and i-butanol; ketones, such as, for example, acetone and methyl ethyl ketone; ethers, such as, for example, diethyl ether; glycol ethers, such as, for example, ethylene glycol monomethyl ether and ethylene glycol dimethyl ether, and mixtures of various solvents, and in particular also with water.

If the compound of the formula Ia is employed in the pure optically active form in the transesterification with the alcohol R$^3$OH, the compound of the formula Ib is likewise obtained in the pure optically active form in the transesterification, and in particular, starting from compounds Ia with R$^4$=(S)—CH(CH$_3$)COOR$^5$, as a rule dextrorotatory isomers of the formula Ib are obtained, and starting from compounds Ia where R$^4$=(R)—CH(CH$_3$)COOR$^5$, as a rule laevorotatory isomers of the formula Ib are formed, and starting from compounds of the formula Ia where R$^4$=2—O—(R$^5$-carbonyl)-isosorbid-5-yl, as a rule the laevorotatory isomers of the formula Ib are formed.

If they have basic substituents, the optically active 1,4-dihydropyridine derivatives of the formula I form acid addition salts with inorganic or organic acids. Inorganic and organic acids are suitable for the formation of such acid addition salts. Examples of suitable acids are: hydrogen chloride, hydrogen bromide, naphthalenedisulphonic acids, in particular naphthalene-1,5-disulphonic acid, phosphoric acid, nitric acid, sulphuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulphamic acid, phenylpropionic acid, gluconic acid, ascorbic acid, isonicotinic acid, methanesulphonic acid, p-toluenesulphonic acid, citric acid or adipic acid. Pharmacologically acceptable acid addition salts are preferred. The acid addition salts are prepared in the customary manner by combining the components, advantageously in a suitable solvent or diluent. In the synthesis of the compounds of the formula I, the acid addition salts may initially be formed in the course of working up. If desired, the free compounds of the general formula I can be obtained from the acid addition salts in a known manner, for example by dissolving or suspending them in water, rendering the solution or suspension alkaline, for example with sodium hydroxide solution, and then isolating the compounds.

The optically inactive compounds of the formula Ib described in European Patent Application No. 83 112 562.0 have interesting cardiovascular actions. As highly active calcium antagonists, they inhibit the contraction caused in the muscle cell by calcium and have a hypotensive and antianginal action, and can thus contribute, for example, towards lowering blood pressure and reducing the load on the heart.

It has now been found that the pharmacological action of the compounds of the formula I is linked to a high degree with the configuration of the chemical compounds, and in particular as a rule the laevorotatory optical isomers are approximately 100 times more effective as calcium antagonists than the corresponding dextrorotatory enantiomers. The laevorotatory optical isomers are therefore as a rule preferred.

The optically active compounds of the formula I and their pharmacologically acceptable acid addition salts can therefore be administered to humans as medicines by themselves, in mixtures with one another or in the form of pharmaceutical formulations, which allow enteral or parenteral administration and contain, as the active constituent, an effective dose of at least one compound of the formula I or an acid addition salt thereof, in addition to the customary pharmaceutically acceptable excipients and additives. The formulations usually contain about 0.5 to 90 percent by weight of the therapeutically active compound.

The medicines can be administered orally, for example in the form of pills, tablets, lacquered tablets, coated tablets, granules, hard and soft gelatine capsules, solutions, syrups, emulsions or suspensions or aerosol mixtures. Administration can also, however, be effected rectally, for example in the form of suppositories, parenterally, for example in the form of injection solutions, or percutaneously, for example in the form of ointments or tinctures.

The pharmaceutical products are prepared in a manner which is known per se, pharmaceutically inert inorganic or organic excipients being used. To prepare pills, tablets, coated tablets and hard gelatine capsules, it is possible to use, for example, lactose, maize starch or derivatives thereof, talc, stearic acid or salts thereof, and the like. Excipients for soft gelatine capsules and suppositories are, for example, fats, waxes, semi-solid and liquid polyols, natural and hardened oils and the like. Examples of suitable excipients for the preparation of solutions and syrups are water, sucrose, invert sugar, glucose, polyols and the like. Examples of suitable excipients for the preparation of injection solutions are water, alcohols, glycerol, polyols, vegetable oils and the like.

Besides the active ingredients and excipients, the pharmaceutical products can also contain additives, such as, for example, fillers, extenders, disintegrating agents, binders, lubricants, wetting agents, stabilisers, emulsifiers, preservatives, sweeteners, colorants, flavouring or aromatising agents, thickeners, diluents and buffer substances, and furthermore solvents or solubilising agents or agents for achieving a depot effect, as well as salts for modifying the osmotic pressure, coating agents or antioxidants. They can also contain two or more compounds of the formula I and/or their pharmacologically acceptable acid addition salts, and in addition other therapeutically active substances.

Examples of such other therapeutically active substances are: $\beta$-receptor blockers, such as, for example, propranolol, pindolol and metoprolol; antianginal agents, such as, for example, carbocromen or molsidomine; tranquillisers, such as, for example, barbituric acid derivatives, 1,4-benzodiazepines and meprobamate; diuretics, such as, for example, chlorothiazide; agents which tonicise the heart, such as, for example, digitalis products; hypotensive agents, such as, for example, hydralazine, dihydralazine and prazosine; clonidine and Rauwolfia alkaloids; agents which reduce the blood level of fatty acids, such as, for example, bezafibrat and fenofibrat; and agents for the prophylaxis of thrombosis, such as, for example, phenprocoumon.

The compounds of the formula I, their pharmacologically acceptable acid addition salts and pharmaceutical products containing the compounds of the formula I or their pharmacologically acceptable acid addition salts as the active compound can be used on humans in combating or preventing diseases which are caused by a flow of calcium into the muscle cells and which can be combated by administration of calcium antagonists. They can thus be employed, for example, as antihypertensive medicines for the various forms of high blood pressure, in combating or preventing angina pectoris and the like, and in the treatment of disorders in cerebral and peripheral blood flow. The dosage can vary within wide limits and is to be adapted to the individual circumstances in each individual case. In general, a daily dose of about 0.01 to 10 mg/kg, preferably 0.05 to 5 mg/kg, of body weight is appropriate for achieving effective results in the case of oral administration. In the case of intravenous administration, the daily dose is in general about 0.001 to 10 mg/kg, preferably 0.01 to 5 mg/kg, of body weight. The daily dose is usually divided into several, for example 2, 3 or 4, part administrations, especially when major amounts are administered. If appropriate, it may be necessary, depending on the individual characteristics, to deviate above or below the stated daily dose.

The $\alpha_D^{20}$ value given in the examples which follow is the specific optical rotation of the substance for polarised light of the sodium D line (589 nm) at 20° C. The solvent used in the measurement and the concentration c in g/100 ml is given, in the examples, in parentheses after the value stated for the specific optical rotation.

EXAMPLE 1

Isopropyl (−)-1,4-dihydro-2,6-dimethyl-3-(1,3,4-oxadiazol-2-yl)-4-(2,3-dichlorophenyl)-pyridine-5-carboxylate (a) Isosorbide 2-acetate 5-acetylacetate 188 g of isosorbide 2-acetate are dissolved in 400 ml of methylene chloride, the solution is prewarmed to 35° C. and 10 ml of triethylamine are added. 84 g of diketene are added dropwise to this mixture so that the internal temperature is between 40° and 45° C. The mixture is then left to stand overnight and concentrated on a rotary evaporator at 40° C.

Yield: 289 g of oil.

(b) Isosorbide 2-acetate 5-aminocrotonate 289 g of crude isosorbide 2-acetate 5-acetylacetate are precooled to 5° to 10° C. in an ice-bath. A solution, precooled to 10° C., of 20 g of ammonia in 250 ml of ethanol is now added, with stirring, so that the internal temperature remains below 25° C. The mixture is then subsequently stirred in an ice-bath for 2 hours, the compound crystallising out. It is filtered off with suction and recrystallised from 500 ml of isopropanol.

Yield: 182 g, melting point=120° C.

(c) 2-(1-(2,3-Dichlorobenzylidene)-acetonyl)-1,3,4-oxadizole 70 g of 2-acetonyl-1,3,4-oxadiazole and 92 g of 2,3-dichlorobenzaldehyde are dissolved in 300 ml of toluene and 5 ml of piperidine are added. The mixture is heated, using a water separator, until no further water separates off. The toluene is stripped off in vacuo and the residue is recrystallised from 250 ml of isopropanol.

Yield: 98 g, melting point=98° to 100° C.

(d) 2-Acetyl-isosorbid-5-yl (−)-1,4-dihydro-2,6-dimethyl-3-(1,3,4-oxadiazol-2-yl)-4-(2,3-dichlorophenyl)-pyridine-5-carboxylate 134 g of 2-(1-(2,3-dichlorobenzylidene)-acetonyl)-1,3,4-oxadiazole and 128 g of isosorbide 2-acetate 5-aminocrotonate are warmed to 80° C. in 300 ml of dimethylformamide for 12 hours. The mixture is concentrated in vacuo at 80° C. and the residue is recrystallised from 500 ml of isopropanol.

Yield: 138 g, melting point=255° to 258°, $\alpha_D^{20}=-45°$ ($CH_2Cl_2$, c=2.0). Still further product can be isolated from the mother liquor.

(e) Isopropyl (−)-1,4-dihydro-2,6-dimethyl-3-(1,3,4-oxadiazol-2-yl)-4-(2,3-dichlorophenyl)-pyridine-5-carboxylate 44.5 g of 2-acetyl-isosorbid-5-yl (−)-1,4-dihydro-2,6-dimethyl-3-(1,3,4-oxadiazol-2-yl)-4-(2,3-dichlorophenyl)-pyridine-5-carboxylate are added to a solution of 2 g of sodium in 150 ml of absolute isopropanol and the mixture is boiled under reflux for 15 hours. It is concentrated under a waterpump vacuum, the residue is poured onto 500 ml of ice-water and the compound is extracted with 500 ml of ethyl acetate. The ethyl acetate phase is extracted by shaking once with a mixture of 200 ml of water and 10 ml of concentrated hydrochloric acid and then with 200 ml of water, dried over $Na_2SO_4$ and concentrated. The residue is recrystallised twice from isopropanol.

Yield: 12 g, melting point=199° to 202° C. $\alpha_D^{20}=-95°$ ($CH_2Cl_2$; c=2.0)

The following compounds can be prepared in an analogous manner:

EXAMPLE 2

Methyl (−)-1,4-dihydro-2,6-dimethyl-3-(1,3,4-oxadiazol-2-yl)-4-(2,3-dichlorophenyl)-pyridine-5-carboxylate Melting point=225° to 229° C., $\alpha_D^{20}=-101°$ ($CH_2Cl_2$; c=1.7)

EXAMPLE 3

Ethyl (−)-1,4-dihydro-2,6-dimethyl-3-(1,3,4-oxadiazol-2-yl)-4-(2,3-dichlorophenyl)-pyridine-5-carboxylate Melting point=187°-189° C. $\alpha_D^{20}=-90°$ ($CH_2Cl_2$; c=2.0)

EXAMPLE 4

Methoxyethyl (−)-1,4-dihydro-2,6-dimethyl-3-(1,3,4-oxadiazol-2-yl)-4-(2,3-dichlorophenyl)-pyridine-5-carboxylate Melting point=192°-195° C. $\alpha_D^{20}=-60°$ ($CH_2Cl_2$; c=1.0)

EXAMPLE 5

Isopropyl (+)-1,4-dihydro-2,6-dimethyl-3-(1,3,4-oxadiazol-2-yl)-4-(2,3-dichlorophenyl)-pyridine-5-carboxylate (a) Ethyl (−)-O-acetylacetyl-(S)-lactate 118 g of ethyl (S)-lactate and 5 ml of triethylamine are dissolved in 300 ml of methylene chloride. 84 g of diketene are slowly added dropwise so that the mixture boils gently. When the addition has ended, the mixture is left to stand at room temperature for 15 hours and is concentrated under a waterpump vacuum, and the residue is distilled:

Boiling point 140° to 145° C./26.7 mbar; yield: 162.9 g. $\alpha_D^{20}=-33°$ ($CH_2Cl_2$; c=2.0).

(b) (S)-1-Ethoxycarbonyl-ethyl (−)-aminocrotonate 80 g of ethyl (−)-O-acetylacetyl-(S)-lactate are dissolved in a solution of 20 g of ammonia in 250 ml of ethanol and the solution is left to stand at room temperature for 20 hours. After the solution has been concentrated under a waterpump vacuum at 40° C., the residue is distilled:

Boiling point 130° to 135° C./2 mbar. Yield 53 g. $\alpha_D^{20}=-77.5°$ ($CH_2Cl_2$; c=2.0).

(c) (S)-1-Ethoxycarbonyl-ethyl (+)-1,4-dihydro-2,6-dimethyl-3-(1,3,4-oxadiazol-2-yl)-4-(2,3-dichlorophenyl)-pyridine-5-carboxylate 30 g of 2-(1(2,3-dichlorobenzylidene)-acetonyl)-1,3,4-oxadizole and 21.3 g of (S)-1-ethoxycarbonylethyl (-)-amino-crotonate are warmed to 80° C. in 100 ml of dimethylsulphoxide for 15 hours. The reaction mixture is poured onto 300 ml of ice-water, whereupon a precipitate separates out, and, after the mixture has been subsequently stirred for 1 hour, the precipitate is filtered off with suction and recrystallised from 500 ml of ethanol:

yield: 28 g, melting point=218° to 22° C., $\alpha_D^{20}=+98°$ ($CH_2Cl_2$; c=2.0).

(d) Isopropyl (+)-1,4-dihydro-2,6-dimethyl-3-(1,3,4-oxadiazol-2-yl)-4-(2,3-dichlorophenyl)-pyridine-5-carboxylate 44 g of (S)-1-ethoxycarbonyl-ethyl (+)-1,4-dihydro-2,6-dimethyl-3-(1,3,4-oxadiazol-2-yl)-4-(2,3-dichlorophenyl)-pyridine-5-carboxylate are added to a solution of 2.2 g of sodium in 400 ml of isopropanol and the mixture is heated under reflux for 20 hours. The mixture is concentrated to a volume of about 150 ml under a waterpump vacuum and the concentrate is poured onto 600 ml of ice-water. The product is extracted three times with 200 ml of diethyl ether each time and the combined ether phases are washed twice more with 300 ml of water each time, dried over sodium sulphate and concentrated under a waterpump vacuum. The residue is stirred with a little diethyl ether and, when the crystallisation has ended, the crystals are filtered off with suction. The solid is recrystallised from thanol/water:

Yield: 10.3 g, melting point=198° to 201° C. $\alpha_D^{20}$=+90° (CH$_2$Cl$_2$; c=3.8).

The following compounds can be prepared in an analogous manner:

EXAMPLE 6

Methyl (+)-1,4-dihydro-2,6-dimethyl-3-(1,3,4-oxadiazol-2-yl)-4-(2,3-dichlorophenyl)-pyridine-5-carboxylate Melting point=225°-228° C. $\alpha_D^{20}$=+105.7° (CH$_2$Cl$_2$; c=1.0).

EXAMPLE 7

2-Methoxyethyl (+)-1,4-dihydro-2,6-dimethyl-3-(1,3,4-oxadiazol-2-yl)-4-(2,3-dichlorophenyl)-pyridine-5-carboxylate Melting point=190°-192° C. $\alpha_D^{20}$=+73° (CH$_2$Cl$_2$; c=0.4).

EXAMPLE 8

Isopropyl (−)-1,4-dihydro-2,6-dimethyl-3-(1,3,4-oxadiazol-2-yl)-4-(2,3-dichlorophenyl)-pyridine-5-carboxylate (a) Ethyl (+)-O-acetylacetyl-(R)-lactate 118 g of ethyl (R)-lactate and 5 ml of triethylamine are dissolved in 300 ml of methylene chloride. 84 g of diketene are slowly added dropwise so that the mixture boils gently. When the addition has ended, the mixture is left to stand at room temperature for 15 hours, and is concentrated under a waterpump vacuum, and the residue is distilled.

Boiling point 140° to 145° C./26.7 mbar; yield: 165 g. $\alpha_D^{20}$=+35° (CH$_2$Cl$_2$; c=2.0).

(b) (R)-1-Ethoxycarbonyl-ethyl (+)-aminocrotonate 80 g of ethyl (+)-O-acetylacetyl-(R)-lactate are dissolved in a solution of 20 g of ammonia in 250 ml of ethanol and the solution is left to stand at room temperature for 20 hours. After cooling, a crystalline precipitate separates out.

Melting point=61°-63° C., yield 65 g. $\alpha_D^{20}$=+75° (CH$_2$Cl$_2$; c=2.0).

(c) (R)-1-Ethoxycarbonyl-ethyl (−)-1,4-dihydro-2,6-dimethyl-3-(1,3,4-oxadiazol-2-yl)-4-(2,3-dichlorophenyl)-pyridine-5-carboxylate 30 g of 2-(1(2,3-dichlorobenzylidene)-acetonyl)-1,3,4-oxadiazole and 21.3 g of (R)-1-ethoxycarbonyl-ethyl (+)-aminocrotonate are warmed to 80° C. in 100 ml of dimethylsulphoxide for 15 hours. The reaction mixture is poured onto 300 ml of ice-water, whereupon a precipitate separates out, and, after the mixture has been subsequently stirred for 1 hour, the precipitate is filtered off with suction and recrystallised from 500 ml of ethanol:

Yield: 28 g, melting point=218° to 220° C., $\alpha_D^{20}$=−100° (CH$_2$Cl$_2$; c=2.0).

(d) Isopropyl (−)-1,4-dihydro-2,6-dimethyl-3-(1,3,4-oxadiazol-2-yl)-4-(2,3-dichlorophenyl)-pyridine-5-carboxylate To dissolve 150 mg of lithium in 100 ml of isopropanol, 10 g of (R)-1-ethoxycarbonyl-ethyl (−)-1,4-dihydro-2,6-dimethyl-3-(1,3,4-oxadiazol-2-yl)-4-(2,3-dichlorophenyl)-pyridine-5-carboxylate are added and the mixture is heated at 110° C. in an autoclave for 2 hours. The mixture is concentrated to ⅓ of the original volume under a waterpump vacuum and the concentrate is poured onto 150 ml of ice-water. The solid product is filtered off with suction and recrystallised from ethanol/water (volume ratio 6:4):

Yield: 5.5 g, melting point =202° to 204° C. $\alpha_D^{20}$=−96° (CH$_2$Cl$_2$; c=2.0).

The following compounds can be prepared in an analogous manner:

EXAMPLE 9

Methyl (−)-1,4-dihydro-2,6-dimethyl-3-(1,3,4-oxadiazol-2-yl)-4-(2,3-dichlorophenyl)-pyridine-5-carboxylate

EXAMPLE 10

Ethyl (−)-1,4-dihydro-2,6-dimethyl-3-(1,3,4-oxadiazol-2-yl)-4-(2,3-dichlorophenyl)-pyridine-5-carboxylate

EXAMPLE 11

Propyl (−)-1,4-dihydro-2,6-dimethyl-3-(1,3,4-oxadiazol-2-yl)-4-(2,3-dichlorophenyl)-pyridine-5-carboxylate

EXAMPLE 12

Butyl (−)-1,4-dihydro-2,6-dimethyl-3-(1,3,4-oxadiazol-2-yl)-4-(2,3-dichlorophenyl)-pyridine-5-carboxylate

EXAMPLE 13

Isobutyl (−)-1,4-dihydro-2,6-dimethyl-3-(1,3,4-oxadiazol-2-yl)-4-(2,3-dichlorophenyl)-pyridine-5-carboxylate

EXAMPLE 14

2-Methoxyethyl (−)-1,4-dihydro-2,6-dimethyl-3-(1,3,4-oxadiazol-2-yl)-4-(2,3-dichlorophenyl)-pyridine-5-carboxylate

EXAMPLE 15

3-Methoxypropyl (−)-1,4-dihydro-2,6-dimethyl-3-(1,3,4-oxadiazol-2-yl)-4-(2,3-dichlorophenyl)-pyridine-5-carboxylate

EXAMPLE 16

2-isopropoxy-ethyl (−)-1,4-dihydro-2,6-dimethyl-3-(1,3,4-oxadiazol-2-yl)-4-(2,3-dichlorophenyl)-pyridine-5-carboxylate Melting point=151°-154° C. $\alpha_D^{20}$=−50° (CH$_2$Cl$_2$; c=2.0).

EXAMPLE 17

Cyclopentyl (−)-1,4-dihydro-2,6-dimethyl-3-(1,3,4-oxadiazol-2-yl)-4-(2,3-dichlorophenyl)-pyridine-5-carboxylate

EXAMPLE 18

2-Diethylamino-ethyl (−)-1,4-dihydro-2,6-dimethyl-3-(1,3,4-oxadiazol-2-yl)-4-(2,3-dichlorophenyl)-pyridine-5-carboxylate Melting point=142°-144° C. $\alpha_D^{20}$=−30° (CH$_2$Cl$_2$; c=2.0).

EXAMPLE 19

2-N-Benzyl-N-methylamino-ethyl (−)-1,4-dihydro-2,6-dimethyl-3-(1,3,4-oxadiazol-2-yl)-4-(2,3-dichlorophenyl)-pyridine-5-carboxylate

EXAMPLE 20

Isoamyl (−)-1,4-dihydro-2,6-dimethyl-3-(1,3,4-oxadiazol-2-yl)-4-(2,3-dichlorophenyl)-pyridine-5-carboxylate

EXAMPLE 21

Cyclohexyl (−)-1,4-dihydro-2,6-dimethyl-3-(1,3,4-oxadiazol-2-yl)-4-(2,3-dichlorophenyl)-pyridine-5-carboxylate

EXAMPLE 22

Neopentyl(−)-1,4-dihydro-2,6-dimethyl-3-(1,3,4-oxadiazol-2-yl)-4-2,3-dichlorophenyl)-pyridine-5-carboxylate

EXAMPLE 23

Isopropyl (−)-1,4-dihydro-2,6-dimethyl-3-(1,3,4-oxadiazol-2-yl)-4-(2,3-dichlorophenyl)-pyridine-5-carboxylate The ethanolic mother liquor of Example 5c is concentrated in vacuo. The residue is taken up in 150 ml of diethyl ether and the mixture is stirred at room temperature for 3 days and then at 0° C. for 4 hours. The precipitate which has separated out is filtered off and discarded and the ethereal solution is concentrated, 20 g of a yellow oil remaining, which is (S)-1-ethoxycarbonyl-ethyl (+)-1,4-dihydro-2,6-dimethyl-3-(1,2,4-oxadiazol-2-yl)-4-(2,3-dichlorophenyl)-pyridine-5-carboxylate, $\alpha_D^{20} = +27.7°$ (CH$_2$Cl$_2$; c=2.0).

This product is transesterified as described in Example 5d and gives 7.5 g of solid.

Melting point=199°-201° C. $\alpha_D^{20} = -91°$ (CH$_2$Cl$_2$; c=2.0).

Pharmacuetical products are described in the following examples:

EXAMPLE 24

Soft gelatine capsules containing 5 mg of active compound per capsule:

|  | per capsule |
|---|---|
| Active compound of the formula I | 5 mg |
| Triglyceride mixture fractionated from coconut oil | 150 mg |
| Capsule contents | 155 mg |

EXAMPLE 25

Injection solution containing 1 mg of active compound per mole:

|  | per ml |
|---|---|
| Active compound of the formula I | 1.0 mg |
| Polyethylene glycol | 0.3 ml |
| Sodium chloride | 2.7 mg |
| Water for injection purposes to | 1.0 ml |

EXAMPLE 26

Emulsion containing 10 mg of active compound per 5 ml:

|  | per 100 ml |
|---|---|
| Active compound of the formula I | 0.2 g |
| Neutral oil | q.s. |
| Sodium carboxymethylcellulose | 0.6 g |
| Polyoxyethylene stearate | q.s. |
| Pure glycerol | 0.2 to 2.0 g |
| Flavour substance | q.s. |
| Water (demineralised or distilled) to | 100 ml |

EXAMPLE 27

Rectal drug form containing 8 mg of active compound per suppository

|  | per suppository |
|---|---|
| Active compound of the formula I | 8 mg |
| Suppository base mass to | 2 g |

EXAMPLE 28

Tablets containing 5 mg of active compound per tablet

|  | per tablet |
|---|---|
| Active compound of the formula I | 5 mg |
| Maize starch (white) | 150 mg |
| Lactose | 60 mg |
| Microcrystalline cellulose | 50 mg |
| Polyvinylpyrrolidone | 20 mg |
| Magnesium stearate | 2 mg |
| Sodium carboxymethyl-starch | 25 mg |
|  | 312 mg |

EXAMPLE 29

Coated tablets containing an active compound according to the invention and another therapeutically active substance

|  | per coated tablet |
|---|---|
| Active compound of the formula I | 6 mg |
| Propanolol | 40 mg |
| Lactose | 90 mg |
| Maize starch | 90 mg |
| Secondary calcium phosphate | 34 mg |
| Soluble starch | 3 mg |
| Magnesium stearate | 3 mg |
| Colloidal silicic acid | 4 mg |
|  | 270 mg |

EXAMPLE 30

Coated tablets containing an active compound according to the invention and another therapeutically active substance

|  | per coated tablet |
|---|---|
| Active compound of the formula I | 6 mg |
| Molsidomine | 5 mg |
| Lactose | 90 mg |
| Maize starch | 90 mg |
| Secondary calcium phosphate | 34 mg |

-continued

|  | per coated tablet |
| --- | --- |
| Soluble starch | 3 mg |
| Magnesium stearate | 3 mg |
| Colloidal silicic acid | 4 mg |
|  | 235 mg |

EXAMPLE 31

Capsules containing an active compound according to the invention and another therapeutically active substance

|  | per capsule |
| --- | --- |
| Active compound of the formula I | 10 mg |
| Prazosine | 5 mg |
| Maize starch | 185 mg |
|  | 200 mg |

The calcium-antagonistic action of the compounds of the formula I has been determined by a modified method of Godfraind and Kaba (Arch. Int. Pharmacodyn. Ther. 196 (Suppl) 35 to 49, 1972) and of Schümann et al (Naunyn-Schmiedeberg's Arch. Pharmacol. 289, 409 to 418, 1975). In these experiments, spiral strips of the arteria pulmonalis of guineapigs are depolarised with 40 mmol of potassium, after equilibration in calcium-free Tyrode's solution. The addition of 0.5 mmol of $CaCl_2$ then triggers off contraction. The relaxing effect of the test substance is determined by cumulative addition in ½ log 10 graduated concentrations. The concentration of the test substance which inhibits the contraction by 50% (=$IC_{50}$, mole/l) is determined from the concentration/effect curve (abscissa: -log mole/l of test substance, ordinate: % inhibition of the maximum contraction, mean value of 4 to 6 vascular strips). The $IC_{50}$ values thus obtained are given in the table which follows. As comparison with the $IC_{50}$ value of $3\times 10^{-9}$ for the known compound nifedipine (=methyl 1,4-dihydro-2,6-dimethyl-4-(2-nitrophenyl)-pyridine-3,5-dicarboxylate), compare German Patent Application No. 1,670,827, shows the values are in some cases considerably more advantageous for the compounds of the formula I.

TABLE

| Compound of the formula I according to Example | $IC_{50}$ (mole/l) |
| --- | --- |
| 1e | $4 \times 10^{-11}$ |
| 2 | $2 \times 10^{-10}$ |
| 3 | $7 \times 10^{-11}$ |
| 4 | $3 \times 10^{-10}$ |
| 8c | $4 \times 10^{-11}$ |
| 16 | $1 \times 10^{-10}$ |

What is claimed is:

1. Isopropyl 1,4-dihydro-2,6-dimethyl-4-(2,3-dichlorophenyl)-3-(1,3,4-oxadiazol-2-yl)-pyridine-5-carboxylate in optically active laevo-rotatory form.

2. (2-Methoxy-ethyl)-1,4-dihydro-2,6-dimethyl-4-(2,3-dichlorophenyl)-3-(1,3,4-oxadiazol-2-yl)-pyridine-5-carboxylate in optically active laevo-rotatory form.

3. Ethyl 1,4-dihydro-2,6-dimethyl-4-(2,3-dichlorophenyl)-3-(1,3,4-oxadiazol-2-yl)-pyridine-5-carboxylate in the optically active laevo-rotatory form.

4. Methyl 1,4-dihydro-2,6-dimethyl-3-(1,3,4-oxadiazol-2-yl)-4-(2,3,-dichloro-phenyl)-pyridine-5-carboxylate in optically active laevorotatory form.

5. ((R)-1-Ethoxycarbonyl-ethyl)-1,4-dihydro-2,6-dimethyl-3-(1,3,4-oxadiazol-2-yl)-4-(2,3-dichlorophenyl)-pyridine-5-carboxylate in optically active laevo-rotatory form.

6. (2-Isopropoxy-ethyl)-1,4-dihydro-2,6-dimethyl-3-(1,3,4-oxadiazol-2-yl)-4-(2,3-dichlorophenyl)-pyridine-5-carboxylate in optically active laevorotatory form.

* * * * *